United States Patent
Schwalenberg et al.

[19]

[11] Patent Number: 5,876,740
[45] Date of Patent: Mar. 2, 1999

[54] WEATHER RESISTANT, SWEET CORN-BASED RODENTICIDAL BAIT AND METHOD OF MANUFACTURING SAME

[75] Inventors: Lee D. Schwalenberg, Waterloo; Ed Eades, Middleton, both of Wis.; Raymon W. Lush, Bloomfield, Nebr.

[73] Assignees: HACCO, Inc., Randolph, Wis.; Sweet Corn Products Co., Bloomfield, Nebr.

[21] Appl. No.: 908,401

[22] Filed: Aug. 7, 1997

[51] Int. Cl.⁶ .................................................. A01N 25/10
[52] U.S. Cl. ........................... 424/408; 424/84; 424/405; 424/409; 424/410; 424/442; 514/458; 514/457
[58] Field of Search .............................. 424/84, 405–410, 424/442, 488; 514/457, 456, 357

[56] References Cited

U.S. PATENT DOCUMENTS

| | | | |
|---|---|---|---|
| 3,943,893 | 10/1974 | Burlow | 424/84 |
| 4,581,378 | 4/1986 | Lazar et al. | 514/681 |
| 4,815,923 | 3/1989 | Lush | 424/410 |

OTHER PUBLICATIONS

Zeneca Professional Products, Zeneca Inc., "Brodifacoum Concentrate II," published on or before Jul. 1997.
California Pellet Mill Co., San Francisco, CA, "Questions you should ask before you buy a pellet mill:", publ. on or before Jul. 1997.
California Pellet Mill Co., San Francisco, CA, "Series CL, Laboratory Pellet Mills," © 1997.
California Pellet Mill Co., San Francisco, CA, "Processing the harvest for more than a century," © 1995.
California Pellet Mill Co., San Francisco, CA, "Series C Proces pellet mills" © 1983.
Farnam Companies, Inc., Omaha, NE, "Just One Bite," © 1993.
Motamca, Clearwater, FL, "Hawk Bait Chunx", publ. on or before Jul. 1997.

*Primary Examiner*—Neil S. Levy
*Attorney, Agent, or Firm*—Carol W. Burton, Esq.; Holland & Hart LLP

[57] ABSTRACT

A weather resistant, rodenticidal bait comprises sweet corn flour, an effective amount of a rodenticide, and water. Additional preferred ingredients include a glutinous flour, flavoring and salt. Preferred rodenticides include diphacinone, brodifacoum, warfarin, bromadialone, bromethalin and their functional equivalents. A preferred method of manufacturing the weather resistant rodenticidal bait of the present invention utilizes cold extrusion techniques. The most preferred method of manufacturing includes the steps of mixing a sweet corn flour, an effective amount of a rodenticide, and water to produce a rodenticidal mixture. In the preferred method, a glutinous flour is also mixed with the sweet corn flour, with wheat flour the most preferred glutinous flour. The rodenticidal mixture is forced through an extrusion chamber and out a nozzle opening, to produce extruded chunks. The extruded chunks are preferably dried to obtain weather resistant, sweet corn-based rodenticidal bait having a sweet corn content of at least 65% by weight of the weather resistant bait and a moisture content of not more than 10% by weight of the weather resistant bait.

11 Claims, 2 Drawing Sheets

WEATHER RESISTANT, SWEET CORN-BASED RODENTICIDAL BAIT AND METHOD OF MANUFACTURING SAME

FIELD OF THE INVENTION

The present invention relates to rodenticidal bait compositions. More particularly, the present invention relates to weather resistant, rodenticidal bait compositions having satisfactory rodent acceptability and to methods of manufacturing same.

BACKGROUND OF THE INVENTION

Rodenticidal baits typically include a carrier and a rodenticide. The rodenticide is the active ingredient and the carrier is often referred to as an inert ingredient. In most rodenticidal baits, the carrier is really not chemically inert, in that it typically contains one or more grains or other foods which are attractive to rodents. The carrier does not, however, typically contribute to the rodenticidal activity of the bait, and thus is inert in that respect.

U.S. Pat. No. 4,815,923 for SWEET CORN BASED RODENTICIDE to Raymon W. Lush issued Mar. 28, 1989 and discloses a rodenticidal bait which includes an active ingredient mixed with an inert ingredient comprising dried sweet corn as a substantial portion thereof. The '923 patent recites that the optimal particle size of the ground corn for such use with Norway and roof rats is between 0.5 mm and 1.5 mm in diameter. In addition, the '923 patent contemplates using ground sweet corn of this grind to form rodenticidal pellets of approximately 3/16 inch in diameter. Experience has shown that such pellets have an average bulk density of less than 45 lbs/ft$^3$. Rodenticidal efficacy tests disclosed in the '923 patent indicated that when test rats were presented with such pellets and with a challenge bait containing 65% yellow dent corn, 25% rolled oats, 5% corn oil and 5% white sugar but no active ingredient, the pellets containing an active ingredient constituted over one half of the rats' diet and resulted in a 100% mortality rate.

However, unlike test settings where rats, mice or other rodents are maintained in cages or other controlled environments, rodent control is often required in and around barns, silos and other outbuildings which are subject to varying weather conditions. Under such conditions, rodenticidal baits which are not weather resistant are likely to disintegrate and/or turn moldy, with the bait becoming less attractive to rodents and the active ingredient susceptible to leaching and dissolution into water flowing into the surrounding area. Long term rodent control under such conditions necessarily requires frequent bait replacement.

One conventional pellet manufacturing technique for sweet-corn rodenticidal pellets utilizes a pelletizing mill 8 like that schematically shown in FIG. 1. The mill 8 includes a drum 10 having a pelleting cavity 12 in which are positioned rollers 14. Formed in drum 10 and extending from the inside wall 16 of drum 10 to the outside wall 18 thereof are a plurality of radial die holes 20, with one or more knives 22 positioned adjacent outside wall 18. To produce rodenticidal pellets, material 24 to be pelleted is fed continuously into pelleting cavity 12 while drum 10 is rotated. Rotation of drum 10 causes rollers 14 to turn in the same direction, with two wedges 26 of material 24 formed thereby. Material 24 is compressed by the wedging action of drum 10 and rollers 14, forced through die holes 20, and sheared by knives 22 to form rodenticidal pellets 28.

While the pelletizing technique described above does involve the application of pressure to form rodenticidal pellets, the density of such pellets is typically sufficient only to prevent excessive pellet attrition and dust formation during pellet packaging, shipping and distribution. Pellet density is typically not consistent enough to overcome a tendency of the pellets to disintegrate in a wet environment. It appears that lack of precise control over the length of time the material to be pelleted stays in the die holes may contribute to variable pellet density.

Weather resistant rodenticidal baits are available. However, many conventional weather resistant baits include wax to provide a weather resistant quality. Incorporating wax can be problematic for at least two reasons. First, elevated temperatures required for wax liquefaction can be detrimental to some rodenticides due for certain active ingredients which degrade at elevated temperatures. Second, even with rodenticides which are stable at elevated temperatures, rodenticidal baits containing wax are typically less attractive to the target rodents than wax-free rodenticidal baits. Decrease in attractiveness to the rodents is especially problematic with rodenticides requiring multiple feedings by a rodent. Attractiveness must be maintained for the rodent to return to ingest sufficient rodenticide.

It is against this background that the significant improvements and advancements of the present invention have taken place.

OBJECTS OF THE INVENTION

It is the principal object of the present invention to provide a weather resistant rodenticidal bait.

It is another object of the present invention to provide such a rodenticidal bait in which attractiveness to rodents is maintained under adverse weather conditions.

It is a further object of the present invention to provide a rodenticidal bait having the aforementioned qualities, which is wax-free and economical to manufacture.

It is a yet further object of the present invention to provide a method of manufacturing such a rodenticidal bait in which the active ingredient is not subject to uncontrolled degradation during manufacturing.

SUMMARY OF THE INVENTION

In accordance with the present application, a weather resistant, sweet corn-based rodenticidal bait comprises compressed chunks of a rodenticidal mixture comprising ground sweet corn flour, water, and an effective amount of a rodenticide. The mixture may optionally contain a glutinous flour, for example wheat, rice, alfalfa or oat flour. Preferably, the chunks are compressed to an average bulk density of at least 50 lbs/ft$^3$, more preferably to an average bulk density of from at least 55 lbs/ft$^3$ to 60 lbs/ft$^3$. In the preferred embodiment, sweet corn flour constitutes at least 65% by weight of the bait. In the most preferred embodiment, wheat flour constitutes at least 15% by weight of the bait. Preferred rodenticides include diphacinone, brodifacoum, warfarin, bromadialone, bromethalin and their functional equivalents.

A preferred method of manufacturing the weather resistant, sweet corn-based rodenticidal bait of the present invention initially involves the mixing of ground sweet corn flour with a rodenticide and water to produce a rodenticidal mixture. The rodenticidal mixture is conducted through an extrusion chamber and, under pressure, out a nozzle opening which is smaller in cross sectional area than the chamber, to produce extruded, compressed rodenticidal chunks having a preferred moisture content of at most 15% and an average bulk density of at least 50 lbs/ft$^3$, more preferably an average bulk density of from at least 55 lbs/ft$^3$ to 60 lbs/ft$^3$. The chunks are most preferably dried a moisture content of from approximately 10% to 13% to form the weather resistant, sweet corn-based rodenticidal bait of the present invention. Preferably, after addition of water, a sticky material is formed which under the pressure of extrusion, creates a dense, tightly bound chunk having a glossy, weather resistant coat. For optimal consistency and attractiveness to rodents, glutinous ground flour such as wheat, alfalfa, oat or rice flour is mixed with the sweet corn flour.

A more complete appreciation of the present invention and its scope can be obtained from the following detailed description of presently preferred embodiments of the invention, and the appended claims.

DETAILED DESCRIPTION OF THE INVENTION

In accordance with the present application, a weather resistant sweet corn rodenticidal bait comprises compressed chunks of a rodenticidal mixture which includes ground sweet corn flour, water, and an effective amount of a rodenticide. The mixture optionally may also contain a glutinous flour, for example wheat, rice, alfalfa or oat flour. Preferably, the sweet corn flour constitutes at least 65% by weight of the chunks and wheat flour constitutes at least 15% by weight of the chunks. Preferably, the chunks are compressed to an average bulk density of at least 50 lbs/ft$^3$, more preferably to an average bulk density of from at least 55 lbs/ft$^3$ to 60 lbs/ft$^3$. Preferred rodenticides include diphacinone, brodifacoum, warfarin, bromadialone, bromethalin and their functional equivalents.

EXAMPLE I

In a preferred method of manufacturing the weather resistant, sweet corn rodenticidal bait of the present invention, 18 pounds of medium grind whole durham wheat flour ½ pound of salt, 69.8 pounds of dried sweet corn having a moisture content of approximately 10%, and 0.05 pounds of polychloro copper phthalocyanine dye (Zulu green standard shade 3824 dye available from Englehard Corporation, of Iselin, N.J.), were mixed for approximately 10 minutes. While mixing, 0.0005 pounds of caramel flavoring (product no. 2679 from Agrimerica of Northbrook, Ill.) and 10 pounds of water were slowly added, resulting in a mixture having a sticky, paste-like consistency. Thereafter, 1.7 pounds of brodifacoum concentrate (0.25% 3-[3-(4'-bromo[1,1'-biphenyl]4-yl)-1,2,3,4-tetra-hydro-1-naphthalenyl]4-hydroxy 2H-1-benzopyran-2-one) available from Zeneca, Inc. of Wilmington, Del., was added over a 2–3 minute period, and the mixture further mixed for approximately 10 minutes to form a rodenticidal mixture. The rodenticidal mixture was fed into a hopper which guided it into a live bottom bin of a cold extruder 30 like that shown in the top plan view of FIG. 2.

Figure 1:
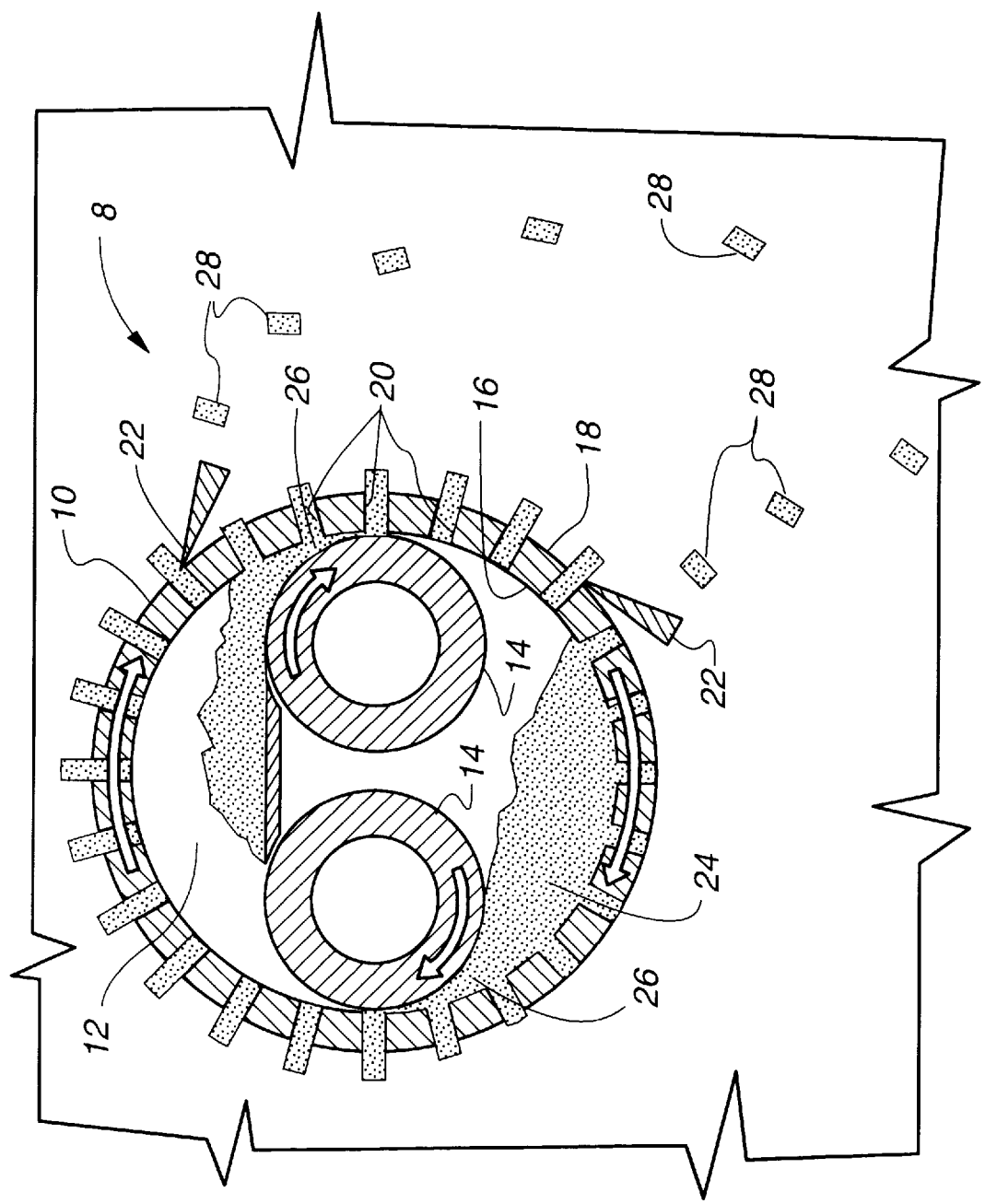
FIG. 1 is a schematic vertical section of a pelletizing mill used to produce conventional sweet-corn based rodenticidal pellets.
Figure 2:
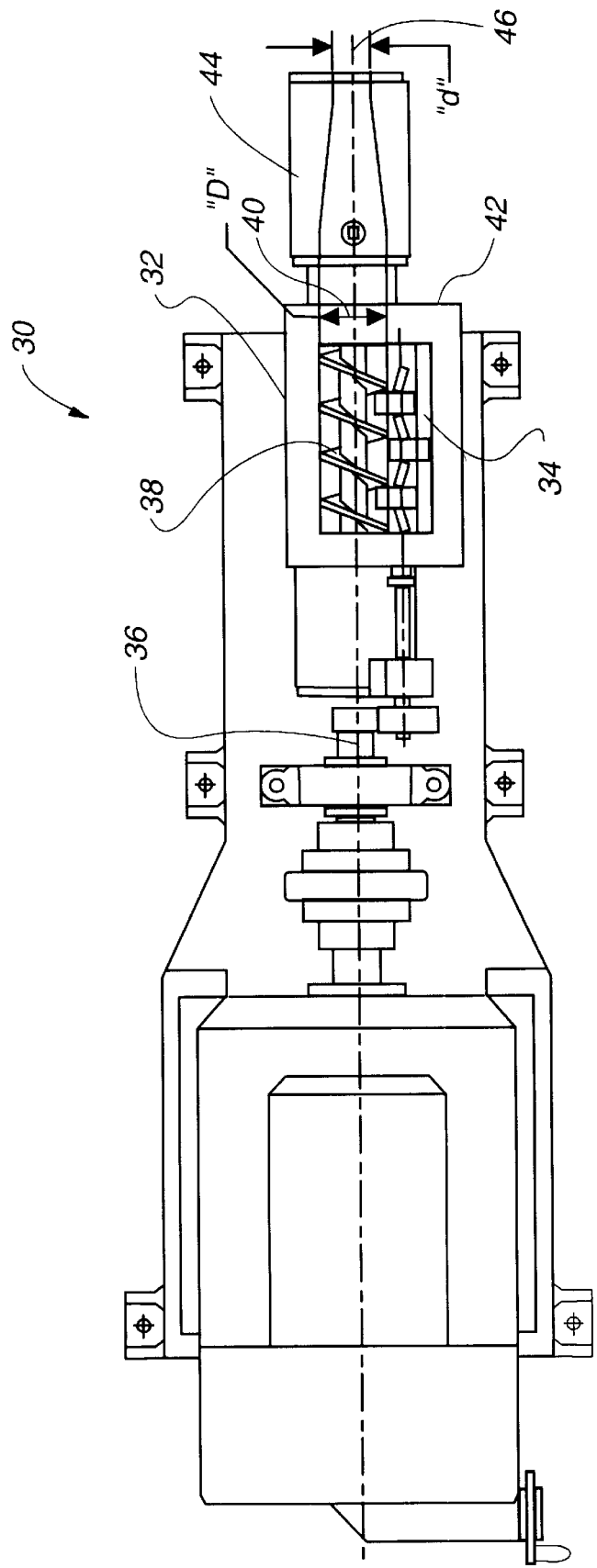
FIG. 2 is a top plan view of a cold extruder used to practice the manufacturing method of the present invention.

Referring now to FIG. 2, it can be seen that the cold extruder 30 includes a housing 32 defining a longitudinal auger chamber 34. Positioned in the chamber 34 along the longitudinal axis thereof, and driven by a drive shaft 36 is an auger 38. Chamber 34 extends to a channel 40 of an cross-sectional diameter "D" formed at a forward end 42 of extruder 30, on which is mounted a nozzle 44 having an opening 46. Opening 46 has a cross-sectional diameter "d", which is substantially less than the average cross-sectional diameter "D" of channel 40. In the preferred manufacturing method of the present invention, the average cross-sectional diameter "D" of channel 40 is approximately 4", while the cross-sectional diameter "d" of opening 46 is 1". As the rodenticidal mixture is forced by the auger 38 along chamber 34, into channel 40, and out nozzle 44, a compressed rope of rodenticidal mixture is extruded, predetermined lengths of which are cut with a knife of a cutting assembly.

The housing 32 of the cold extruder 30 and nozzle 44 are preferably operated at ambient temperature, with neither heating nor cooling of cold extruder components. It is understood that while some heat is generated in the nozzle 44 by the friction of the rodenticidal material as it is forced along and out the nozzle 44, the resulting temperature increase in the rodenticidal material is not sufficient to either cook the bait or substantially degrade the active ingredient. The chunks, which initially have a moisture content of approximately 15%, are then dried to form the weather resistant, sweet corn-based rodenticidal bait of the present invention, preferably to a moisture content of from approximately 13% to 10% and an average bulk density of at least 50 lbs/ft$^2$. A most preferred average bulk density range of the bait is from 55 lbs/ft$^2$ to 60 lbs/$^2$.

The weather resistant, sweet corn-based, rodenticidal bait resulting therefrom have a glossy sheen and been shown to maintain rodenticidal functionality and rodent acceptability even after 15 days of 90% to 100% humidity and 100° F. temperature. Although the chemical structure which is responsible for the glossy sheen of the weather resistant, sweet corn-based rodenticidal bait of the present invention is not known, it is believed that the glossy appearance may result from migration of oils and/or lipids in the rodenticidal mixture between grains to the surface of the extruded chunks, possibly as a result of the pressure of the extrusion process, laminar flow of constituent grains, and/or the slight temperature increase of the mixture resulting from frictional engagement of mixture contacting the inner surface of the extruder nozzle. Such oils and/or lips, which are less easily dissolved in water than the sugar and other constituents in the bait, are believed to form a protective coating giving the present invention much of its weather resistant quality.

To test rodent acceptability of the rodenticidal bait of the present invention, single day tests were conducted with mice and rats. In each case, the EPA standard Rat and Mouse Challenge diet of 65.0% by weight whole yellow ground cornmeal, 25.0% by weight rolled oat groats, 5.0% by weight powdered sugar and 5.0% by weight corn oil was mixed and placed in a glass container in a cage containing either five mice or a single rat.

Comparison tests were run for both rats and mice. In each test, 10 males and 10 females were offered the Challenge Diet and either (i) alone—the control; or with (ii) fresh, weather resistant, sweet corn-based rodenticidal bait of the present invention, or (iii) weather resistant, sweet corn-based rodenticidal bait of the present invention which had been previously weatherized for 15 days. Weatherization consisted of maintaining the bait in an approximately 100° F. environment with a humidity of approximately 90% to 100%. Fresh bait mortality was considered acceptable if it resulted in at least 90% mortality. Weatherized bait mortality was considered acceptable if it resulted in at least 80% mortality. Test results are summarized in Table I.

TABLE I

| ANIMAL | DIETS AVAILABLE | MORTALITY % |
|---|---|---|
| Rats | Challenge diet + fresh Example I bait | 95% |
| Rats | Challenge diet + weatherized Example I bait | 90% |
| Rats | Challenge diet | 0% |
| Mice | Challenge diet + fresh Example I bait | 90% |
| Mice | Challenge + weatherized Example I bait | 90% |
| Mice | Challenge diet | 0% |

Both the fresh and weatherized baits of the present invention exhibited acceptable mortality rates. The weatherized bait maintained physical integrity despite the 15-day weatherizing treatment, and it is believed that the physical integrity may have contributed to the consistent acceptability levels of both fresh and weatherized baits exhibited by the rodents. Despite the absence of wax, the rodenticidal bait of the present invention is able to maintain an acceptable level of rodent mortality over time.

To compare acceptability among rodents of the preferred rodenticidal bait of the present invention with other baits, groups of 20 rats and 20 mice were presented with rodenticidal bait made in accordance with Example I above and an alternative bait. In a first test, bait commercially available from Farnam Companies, Inc. of Omaha, Nebr. 68112, under the tradename "Just-One-Bite" was used. The label for this product instructs the user to "Protect bait from rain or snow", "Maintain an uninterrupted supply of fresh bait for at least 10 days or until fresh signs of rat activity cease to appear" and "Maintain an uninterrupted supply of fresh bait for at least 15 days or until fresh signs of mice activity cease to appear". It is believed that this bait is not a weather resistant bait. In a second test, bait commercially available from Motomco Ltd. of Clearwater, Fla. 34615 under the tradename "Hawk Bait Chunx was used. The Hawk® package label instructs the user to "Maintain an uninterrupted supply of fresh bait for at least 10 days or until signs of rat activity cease" and "Maintain an uninterrupted supply of fresh bait for at least 15 days or until signs of rat activity cease". It is believed that Hawk Bait Chunx is not a weather resistant bait. In a third test, a weather resistant bait containing grain and wax was used. Test results are summarized in Table II.

TABLE II

| Animal | Description of Alternative Bait | Example I Bait as % Total Diet | Alternative Bait as % Total Diet |
|---|---|---|---|
| Rats | Example I + Just-One-Bite | 59.46% | 40.54% |
| Mice | Example I + Jusr-One-Bite | 44.54% | 55.46% |
| Rats | Example I + Hawk | 52.49% | 47.51% |
| Mice | Example I + Hawk | 48.76% | 51.24% |
| Rats | Example I + grain/wax bait | 64.03% | 35.97% |
| Mice | Example I + grain/wax bait | 54.02% | 45.98% |

The data appear to indicate that the preference of the rodents tested for the weather resistant Example I bait as compared to the Just-One-Bite bait was mixed (e.g., rats as a whole, ate more Example I bait, mice as a whole ate more Just-One-Bite bait). The preference of the rodents tested for the weather resistant Example I bait as compared to the Hawk bait also appeared to be mixed (e.g., rats as a whole ate more Example I bait, mice as a whole ate more Hawk bait). However, as a group, the rats and mice tested evidenced a preference for the weather resistant Example I bait over the weather resistant bait containing grain and wax (e.g., both the rates and the mice, taken as a whole, ate more Example I bait than the grain/wax bait).

Although brodifacoum was used above in manufacturing the Example I bait, and brodifacoum is presently a preferred rodenticide for use with the composition and manufacturing method of the present invention because of its increased toxicity to rodents, it is understood that the choice of rodenticide will depend upon the physiology of the target rodents, applicable laws and regulations, and other factors. So, for example, while warfarin is less toxic and thus considered safer for other mammals, rodents are known to develop an immunity over generations to warfarin, and if individual rodents do not ingest a sufficient amount of such rodenticides, they will not be eradicated. Because of brodifacoum's substantially increased toxicity, the likelihood of rodents developing a resistance to lethal doses in diminished, and thus are often preferred. Although not most preferred, other rodenticides acceptable for use in practicing the present invention include diphacinone, warfarin, bromadialone, bromethalin and their functional equivalents, together with functional equivalents of brodifacoum.

Presently preferred embodiments of the present invention and many of its improvements have been described with a degree of particularity. It should be understood that this description has been made by way of preferred examples, and that the invention is defined by the scope of the following claims.

What is claimed is:

1. A method of manufacturing a weather resistant, sweet corn-based rodenticidal bait consisting essentially of the steps of:

cold mixing sweet corn flour, an anticoagulant rodenticide and water to produce a rodenticidal mixture, wherein the sweet corn flour constitutes at least 65% by weight of the weather resistant sweet corn-based rodenticidal bait and the mixture optionally includes a glutinous flour and optionally includes caramel flavoring;

cold extruding said rodenticidal mixture under pressure to produce uncooked chunks; and drying the uncooked chunks to produce a weather resistant, sweet corn-based rodenticidal bait having an average bulk density of at least 50 lbs/ft$^3$.

2. The method of claim 1 wherein a glutinous flour selected from the group consisting of wheat flour, alfalfa flour, oat flour and rice flour is mixed in the mixing step with the sweet corn flour, rodenticide and water to produce the rodenticidal mixture.

3. The method of claim 2 wherein the glutinous flour constitutes at least 15% by weight of the weather resistant, sweet corn-based rodenticidal bait, and the average bulk density is at least 55 lbs/ft$^2$.

4. The method of claim 3 wherein the glutinous flour is a wheat flour.

5. The method of claim 1 wherein the rodenticide is selected from the group consisting diphacinone, brodifacoum, warfarin, bromadialone, and bromethalin.

6. The method of claim 1 wherein the average bulk density is at least 55 lbs/ft$^2$.

7. A method of manufacturing a weather resistant, sweet corn-based rodenticidal bait comprising the steps of:

cold mixing ground sweet corn flour, an anticoagulant rodenticide and water to produce a rodenticidal mixture, wherein the sweet corn flour constitutes at least 65% by weight of the a weather resistant, sweet corn-based rodenticidal bait and the mixture optionally includes a glutinous flour and optionally includes caramel flavoring;

conducting the rodenticidal mixture through an extrusion chamber of a cold extruder;

extruding the conducted rodenticidal mixture through a necked-down nozzle to produce extruded, compressed rodenticidal chunks having an average bulk density of at least 50 lbs/ft$^3$;

drying said extruded, compressed rodenticidal chunks to produce an uncooked weather resistant, sweet corn-based rodenticidal bait.

8. The method of claim 7 wherein the glutinous flour is selected from the group consisting of wheat four, alfalfa, oat flour and rice flour.

9. The method of claim 7 wherein the glutinous flour is a wheat flour which constitutes at least 15% by weight of the weatherized, sweet corn-based rodenticidal bait, and the rodenticide is selected from the group consisting of diphacinone, brodifacoum, warfarin, bromadialone and bromethalin.

10. The method of claim 8 wherein the glutinous flour is a wheat flour which constitutes at least 15% by weight of the weather resistant, sweet corn-based rodenticidal bait, and the rodenticide is selected from the group consisting diphacinone, brodifacoum, warfarin, bromadialone and bromethalin.

11. The method of claim 8 wherein the average bulk density of the chunks is at least 55 lbs/ft$^3$.

* * * * *